| United States Patent [19] | [11] Patent Number: 4,529,719 |
|---|---|
| Tye | [45] Date of Patent: Jul. 16, 1985 |

[54] MODIFIED CROSSLINKED STROMA-FREE TETRAMERIC HEMOGLOBIN

[76] Inventor: Ross W. Tye, 937 B Rosenstock Rd., Sausalito, Calif. 94965

[21] Appl. No.: 497,454

[22] Filed: May 4, 1983

[51] Int. Cl.[3] .................. A61K 37/00; A61K 35/14; A23J 1/06; C07G 7/00

[52] U.S. Cl. .................................. 514/6; 260/112 B; 260/112 R; 260/112 SR; 424/101

[58] Field of Search ............ 260/112 B, 112 R, 112 S; 424/177, 95, 101; 546/298; 560/143

[56] References Cited

PUBLICATIONS

Tye, Ross W., *Prog. Clin. Biol. Res.* Apr. 1983, vol. 122, pp. 41–49 "Modification of Hemoglobin-Tetrameric Stabilization".
Walder et al., *Biochemistry*, vol. 18, No. 20, 1979, pp. 4265–4270, "Diaspirins that Crosslink β Chains & Hemoglobin . . . ".
Greenburg et al., *Surgery* vol. 36 (1) pp. 13–16 1979, "Intravascular Persistence and Oxygen Delivery . . . ".
Walder, Joseph et al., *J. Mol. Biol.* vol. 141, pp. 195–216 1980, "Development of Antisickling Compounds . . . Binding Site".

*Primary Examiner*—Blondel Hazel
*Assistant Examiner*—Robin Teskin
*Attorney, Agent, or Firm*—Townsend and Townsend

[57] ABSTRACT

Stroma-free deoxy mammalian tetrameric hemoglobin is crosslinked with certain bis diaspirin esters and modified with pyridoxyl-5'-phosphate followed by reduction to produce bis-diamide covalently crosslinked, pyridoxal-5'-phosphate covalently modified tetrameric hemoglobin wherein the crosslinking and modifying bonds occur in the beta cleft. The modified crosslinked stroma-free tetrameric hemoglobin of this invention is a disease-free, oxygen transporting discrete molecular species, free from cell surface antigens, having use as a substitute for transfusion of red blood cells. This modified crosslinked stroma-free hemoglobin is a stable oxygen carrying protein capable of oxygen delivery to perfused tissue and advantageously remaining in the intravascular space.

23 Claims, 3 Drawing Figures

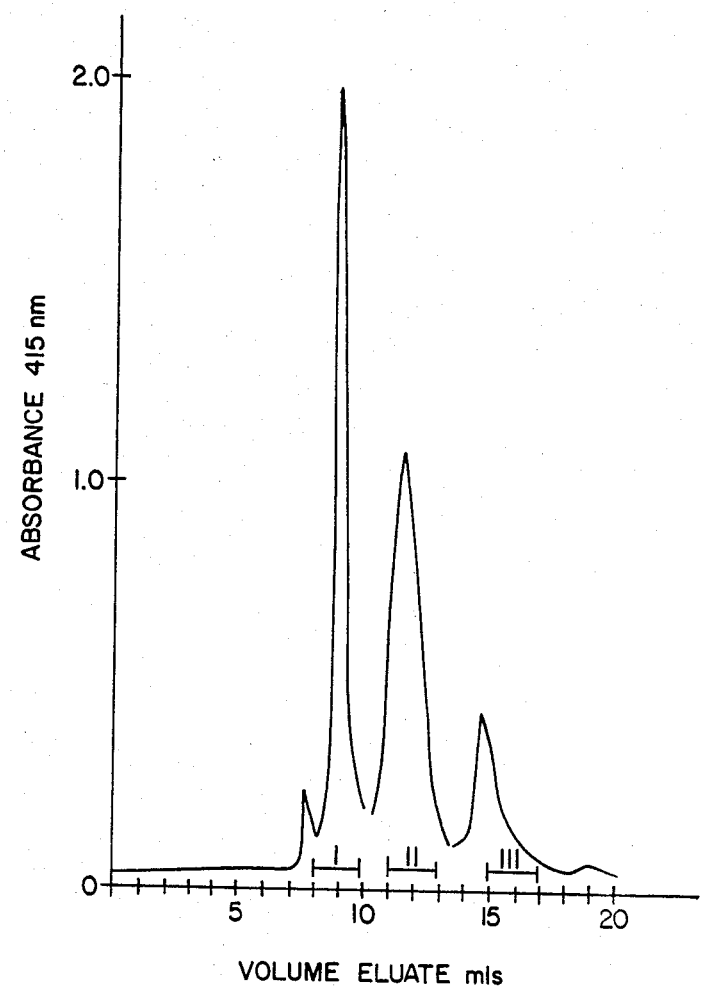
FIG._1.

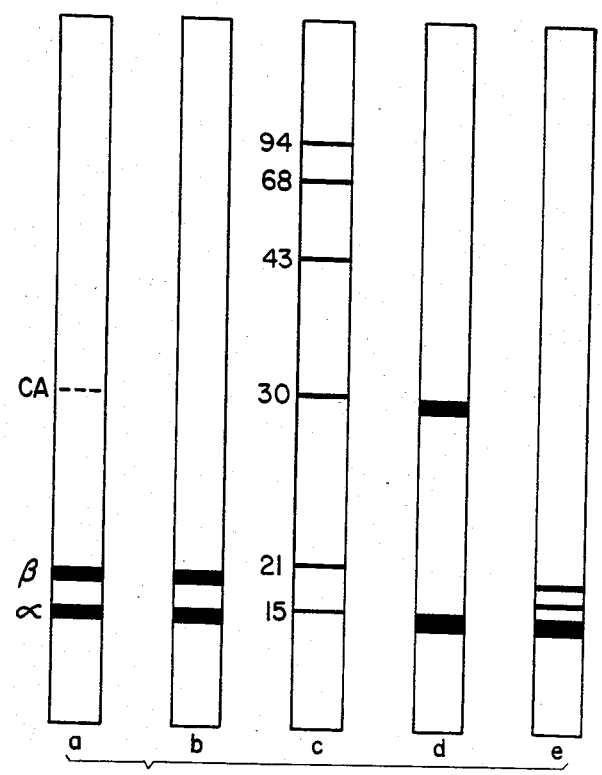
FIG._2.
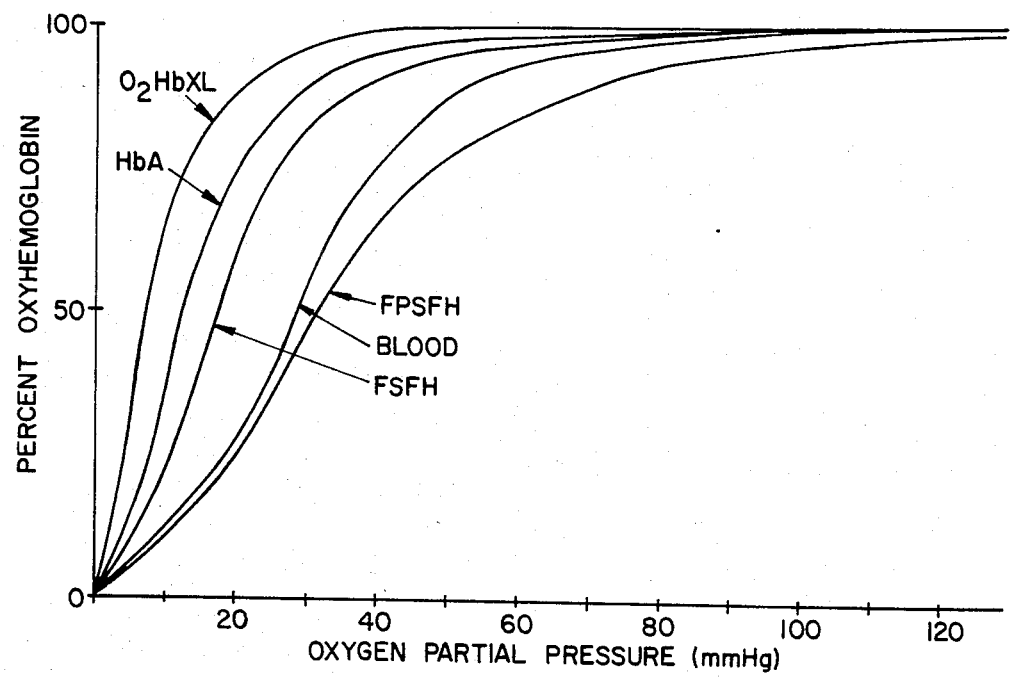
FIG._3.

MODIFIED CROSSLINKED STROMA-FREE TETRAMERIC HEMOGLOBIN

BACKGROUND OF THE INVENTION

Red blood cell substitutes are drugs currently under development for use in oxygen transporting resuscitation fluids and thus decrease the ischemia which may be associated with massive surgery or trauma. This therapeutic approach, in addition to providing volume, crystalloid, colloid and oxygen, may reduce the frequency and severity of the shock syndrome associated with hypovolemic episodes by decreasing both the extent and duration of the ischemia. Used with blood and or packed red blood cells, modified hemoglobin solutions offer increased flexibility in the initial treatment of the hypovolemic episode and prevention of tissue ischemia.

Review of the clinical state intended for treatment with modified hemoglobin solutions includes a brief global view of hypovolemia. Increasing blood loss is initially compensated by increased heart rate and vasoconstriction mediated by the release of catecholamines. Tissue response to a minor reduction in the amount of blood received is to extract a greater portion of the oxygen carried.

As a greater volume of blood is lost, the capacity of the compensatory mechanisms is exceeded. When a critical volume loss is exceeded, the heart is unable to maintain output because of inadequate blood return. If at this point any fluid is given to expand the intravascular volume, the heart will continue to maintain sufficient cardiac output of blood to resume adequate oxygen delivery; however, the penalty is a decreased oxygen transporting ability because of dilution.

Finally with continued loss of blood, even with adequate volume expanders, the hemoglobin concentration falls to levels too low to transport adequate oxygen, and red blood cells or an oxygen-carrying surrogate must be transfused to maintain adequate tissue levels of oxygen.

The quantity of oxygen consumed is the minimum amount required for aerobic metabolism to meet the energy needs for the unit. When oxygen becomes limiting such that the energy requirements can no longer be met, the anerobic pathways are utilized to provide energy. These pathways are much less efficient, unable to meet the energy needs of the cell and produce a metabolic acidosis. The cell, deficient in energy, cannot maintain its membrane potential with the final result of fluid moving from the interstitial space into the intracellular space. The correlation of metabolic acidosis severity is positive with the amount of hypovolemia, its duration, and unsatisfactory resuscitation outcome.

The recommendation of the American College of Surgeons, Committee on Trauma includes the aggressive use of balanced salt solutions (crystalloid) and crossmatched red cells, or type-specific red cells, as clinically indicated during the initial assessment and resuscitation. Supplemental oxygen is encouraged to ensure arterial blood saturation. When appropriate the metabolic acidosis is treated to promote physiological function of hormonal and neural transmitters.

In summary, hypovolemia is an acute event, which soon causes the tissue to become ischemic. The degree, duration, and extent of the ischemia correlate positively with the progression to irreversible shock. Therapeutic intervention includes the correction of the cause for hypovolemia, and vigorous replacement of intravascular fluid similar to that which was lost.

Attempts to replace lost blood with donor blood and crystalloid solutions are standard clinical practice that have evolved during the last fifty years of medicine. Limitations of time, availability, age and viscosity with these solutions have prompted a recent search for still another oxygen carrying resuscitation fluid with the following physiological properties:

(1) Transports adequate amounts of oxygen to the tissue under ambient conditions. The victim inhales ambient air and does not become acidotic; venous oxygen tension stays above 40 mm of Hg.

(2) The solution should be oncotically active as whole blood with a pressure of 25–30 mm of Hg and osmotically active with a value of about 280–300 mOsm.

(3) The solution should have a viscosity equal to that of blood or less as measured in a physiological relevant system.

(4) The retention of the solution within the intravascular space should be a half-disappearance time of 12–48 hours. Most importantly, the mechanism of clearance should not cause an osmotic diuresis (renal) or reticuloendothelial dysfunction (hepatic).

(5) The solution should allow transfusion to all recipients without cross-matching or sensitivity testing.

(6) The solution should be free from disease agents such as bacteria and virus particles (hepatitis, AIDS and others).

(7) Storage properties of the solution or its active oxygen carrier should require minimum amounts of refrigeration and the useful life should be greater than one year.

Obviously the seven properties listed are based upon the desired properties of blood one wishes to keep and a few changes in the underdesired clinical complications encountered that prevent adequate therapy or satisfactory outcome.

An ideal blood substitute with oxygen transport capability must add substantial flexibility to the treatment of hypovolemia as experienced in trauma and massive surgery. First of all it must be immediately available for use in a variety of situations from battlefield to operating room and extracorporeal pump. The ideal product must have minimal acute side effects so that it may be used efficaciously by paramedics with confidence that the diagnostic picture for the subsequent treating physician is not further complicated. It must also be tolerated in large dosages so that adequate therapy does not cause organ system impairment of a delayed or chronic nature. Last but not least, it should not impair our ability to crossmatch blood products for subsequent use as available.

Stroma-Free Hemoglobin

During the last fifteen years since it was first shown that the nephrotoxicity of red blood cell hemolysates was due to the cell wall membranes (stroma) and not due to the hemoglobin there has been a renewed interest in a stroma-free hemoglobin solution as an oxygen transporting resuscitation fluid.

The solution is compatible with aqueous solutions and there is no need to crossmatch the solution since the associated antigens have been removed with the stroma. A ten percent solution is oncotically active, has a lower viscosity than whole blood, and binds 1.34 cc of oxygen as a ligand per gram of hemoglobin at ambient oxygen pressures. The solutions are easily stored and lyophilized preparations endure prolonged storage at room temperature without change in physical chemical properties upon reconstitution with normal saline.

Two features, however, severly limit stroma-free hemoglobin (SFH) as a desired resuscitation fluid. The more important of these is the short intravascular retention in animals due to the filtration of the dimeric Hb($\alpha\beta$) and the profound osmotic diuresis which ensues. This causes a severe compromise in the intravascular volume as the kidney loses the ability to concentrate urine. A less important but significant limitation concerns the level of oxygen maintained by the tissue. Stroma-free hemoglobin binds oxygen so tightly that the tissue oxygen tension is compromised, i.e., the oxygen-SFH ligand is so strong that little if any oxygen is released to the cells at normal tissue oxygen tensions.

Because stroma-free hemoglobin has so many of the ideal properties required for clinical use, work has taken several different approaches to modify the molecular properties that were undersirable.

Modification of Hemoglobin

One of the most attractive ways to circumvent the decreased intravascular retention and the increased oxygen affinity of stroma-free hemoglobin is to modify the covalent structure and thus change the physiologic function. The most widely used modification to decrease the oxygen affinity of hemoglobin is that of pyridoxal-5'-phosphate (PLP) described by Benesch et al. *Biochemistry,* Vol. 11, 3576 (1972). Modification of hemoglobin with this compound introduces a negative charge near a penultimate beta chain histidine and removes a positive charge of the amino terminal end of the same chain. This stabilizes a new molecular configuration similar to the hemoglobin-DPG (diphosphoglycerate) complex with an oxygen affinity similar to that of native hemoglobin within the red cell. The product is known as pyridoxal-5'-phosphate hemoglobin (PLP-hemoglobin), and may have one or two PLP molecules attached per tetramer. PLP-hemoglobin has a satisfactory oxygen affinity but the intravascular retention is still too short to be acceptable as a resuscitation fluid and causes a profound osmotic diuresis.

Some workers have modified PLP-hemoglobin further in an attempt to address the more important issue of intravascular retention. These modifications fall into two broad types of chemical reactions: inter molecular, non-specific crosslinking and inter molecular specific crosslinking.

Most workers have chosen to form the random intermolecular crosslinked polymers of hemoglobin because they believed that the 65,000 Dalton tetramer was filtered by the glomerulus. Thus it seemed rational to at least make dimers of 130,000 Daltons which would not be filtered. Usually the amino groups of lysine on the surface of the hemoglobin molecule are coupled with a bifunctional reagent such as gluteraldehyde or suberimidate. There are 42 lysines available for reaction per hemoglobin tetramer so that one can get an infinite number of different inter intra molecular crosslinks making various polymers of hemoglobin. As the amount of crosslinks formed and the number of tetramers in the polymer increases, the viscosity increases, solubility decreases and the oxygen affinity increases. Intravascular retention in animal models is significantly increased to the desired range. A recent review article, DeVenuto, *Vox Sanguinis,* 44, 129 (1983) contains a more complete description of this and related technology.

The random polymerization is difficult to control and gives a range between two and ten tetramers per polymer. The bigger polymers have greater intravascular retention and greater oxygen affinity. No one has yet standardized an analytical scheme to establish lot to lot variability of structure and function. Many of the investigators use a small molecule to quench the reactions such as lysine, glycine, or ethanolamine. While polymerized pyridoxylated hemoglobin works in exchange transfusion models in the rat, and meets the general requirements of an oxygen transporting fluid, it has a significant viscosity and a profound chemical heterogeneity making it difficult to study as a pharmaceutical agent. Attempts to store this product as a lyophilized powder has failed.

Hemoglobin functions as a tetramer composed of equal numbers of two different protein chains, alpha and beta. The predominant molecular species under physiological conditions is the tetramer $\alpha 2\beta 2$ with a moelcular weight of 65,000. The hemoglobin tetramer may exist in two slightly different conformations. Relaxed (R) or Tense (T) which differ in their oxygen affinity. The two conformations are in equilibrium which may be altered by small molecules such as 2,3-DPG or the presence of ligand. The tense state is enhanced in the absence of ligand and the presence of 2,3-OPG.

R state oxy hemoglobin with a high affinity for ligand exists as an equilibrium between tetramer $\alpha_2\beta_2$ (96%) and dimer $\alpha\beta$ (4%) under physiological conditions. The dimer is composed of one alpha chain and one beta chain, and this association of chains is very strong, so that dissociation into individual monomers does not occur. Crosslinking the alpha chains or the beta chains will prevent dissociation of the tetramer and increase oxygen affinity. It is the dissociation of R state hemoglobin into dimers which allows extra-erythrocytic hemoglobin in the plasma to be filtered by the glomerulus into urine and removed by haptoglobin into the reticuloendothelial system.

The tetrameric structure of T state deoxyhemoplobin has increased stability from six ionic bonds and thus is effectively prevented from dissociation into dimers. In this conformation the beta cleft contact area between the two beta chains (also known as the beta pocket, phosphate pocket and 2-3-diphosphoglycerate binding site) in deoxyhemoglobin is substantially different than in oxyhemoglobin. The changed conformation of the beta cleft in the T state is thought to explain the decreased oxygen affinity stabilized by 2-3-diphosphoglycerate.

Another modification is to place an intramolecular bridge between two like chains of the hemoglobin tetramer. A chemical derivative of hemoglobin was prepared using a compound similar to pyridoxal-5'-phosphate but having the ability to covalently crosslink the beta chains of hemoglobin and stabilize both the conformation with low oxygen affinity and the predominant tetrameric species.

Such an intramolecular crosslinking was reported by Benesch et al., B.B.R.C., 63, 1123 (1975) with the use of 2-nor-2-formyl-pyridoxal-5-phosphate which reacted with hemoglobin in the absence of ligand (oxygen) to form a beta chain bridge. This molecular is not excreted into the urine of rats and has oxygen transport characteristics similar to blood. The hemoglobin modified by 5-norformyl pyridoxal phosphate retains a $P_{50}$ of 26-28 and has an intravascular half disappearance time of 24 hours. The primary route of excretion remains to be determined but, as stated above, the hemoglobin is not found in the urine of the rats. The derivative appears to be clinically acceptable and would merit further testing if the hemoglobin derivative could be prepared in adequate amounts. Unfortunately the compound used for modification is not commercially available and is extremely difficult to prepare. Only 500 mgm of the reagent could be prepared in 3-4 months by an excellent synthetic chemist and the chemical industry has unequivocally said that the reagent cannot be made in large scale. The importance of this derivative lies in the establishment of a unique chemically defined monomer which met all of the physiological established criteria. In essence this derivative demonstrated that chemical modification of hemoglobin to prepare a resuscitation fluid is a realistic concept.

In the context of sickle cell anemia research, Walder et al. in *Biochemistry*, Vol. 18, No. 20, 4265 (1979) utilized bis-diaspirin esters such as bis(3,5-dibromosalicyl)-fumarate and succinate to stabilize the conformation of hemoglobin S with a high oxygen affinity and thereby prevent the tendering to sickle at low oxygen tension. These derivatives have an increased oxygen affinity and appear to diminish the tendency of erythrocytes containing hemoglobin S to sickle at low oxygen tensions.

Walder et al. in Table I, page 4267, reported the results of experiments directed to extent of modification and cross-linking of cell-free HbA by disalicyl succinate and bis(3,5-dibromosalicyl)succinate. These reported results show values of zero and less than five percentage crosslinking, respectively, of deoxy-HbA by these bis-diaspirin reagents.

Similar studies dealing with bis-diaspirin esters are Wood et al., *J. Biol. Chem.*, 256, No. 13, 7046-7052 (1981), Zaugg et al., *J. Biol. Chem.*, 255, No. 7, 2816-2821 (1980), Walder et al., *J. Mol. Biol.*, 141, 195-216 (1980) and Walder et al., *Fed. Proceedings*, 41, 651 (1982).

Additional technology dealing with hemoglobin preparations as blood substitutes is found in the following U.S. patents: U.S. Pat. Nos. 4,336,248 and 4,136,093 to Bonhard et al., 4,061,736 to Morris et al., and 4,053,590; 4,001,401 and 4,001,200 to Bonsen et al.

The present invention relates to a unique modified and crosslinked stroma-free tetrameric hemoglobin, suitable as an oxygen-transporting medium, synthesized by use of certain compounds, pyridoxal-5'-phosphate and a bis-diaspirin ester, in combination to modify and crosslink tetrameric stroma-free deoxy hemoglobin in high yields. It has a significant intravascular retention, adequate oxygen transport capability, and a unique chemical structure.

SUMMARY OF THE INVENTION

This invention is directed to stroma-free tetrameric mammalian hemoglobin covalently crosslinked with a diamide bond-forming moiety derived from a bis-diaspirin ester and covalently modified with pyridoxal-5'-phosphate, wherein the pyridoxal-5'-phosphate covalent modifying bond is in a reduced state and wherein the crosslinking and modifying covalent bonds occur in the beta cleft. More particularly, it is concerned with a human hemoglobin embodiment wherein the hemoglobin to be modified and crosslinked is stroma-free, non-heme protein free deoxy or tense state tetrameric hemoglobin. Also described are inventive embodiments directed to the synthesis of the subject crosslinked modified tetrameric hemoglobin as well as its use in treating a mammal suffering ischemia and/or loss of blood.

Bis-diaspirin-esters useful for the successful practice of this invention in forming in the beta cleft what is believed to be the diamide bond-forming moiety in the crosslinked teterameric hemoglobin have the "ester" or acylating moiety partial structure

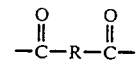

wherein R has a chain length of 1, 2, 3 or 4 units selected from —CH= and —CH$_2$—. Particularly preferred is the fumarate moiety.

The aspirin portion of the crosslinking compound useful in the practice of this invention is to be understood in the conventional sense as having the essential phenolic nucleus ortho substituted with at least the carboxy group.

A preferred class of bis-diaspirin esters according to this invention have the diaspirin moieties selected from a group having the partial structure

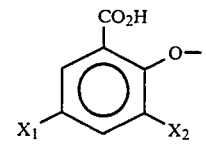

wherein $X_1$ and $X_2$ are selected from —H, —Br, —I, or —NO$_2$ and wherein either $X_1$ or $X_2$ or both are present. It is evident that certain members of this class contain electron withdrawing groups ortho and/or para to the hydroxyl oxygen groups. Particularly preferred is the 3,5-dibromosalicyl moiety.

Stroma-free tetrameric human deoxy hemoglobin (SFH) can be crosslinked using a bis-diaspirin ester such as 3,5-bis-dibromosalicyl-fumarate (BDBF) and modified by pyridoxal-5-phosphate reduced with a mild reducing agent such as NaBH$_4$ to prepare fumaryl-pyridoxal-5'-phosphate stroma free hemoglobin (FPSFH). FPSFH synthesized in this manner is a stable oxygen carrying protein capable of oxygen delivery to perfused tissue $P_{50} \approx 30$, $n \approx 2.2$ and remaining in the intravascular space a half-disappearance time of about 20 hours.

The modified crosslinked tetrameric hemoglobin of this invention offers significant advantages over other potential substitute blood products which include perfluorochemicals, hemosomes, and unmodified hemoglobins. In emergency situtations this product may be superior to whole blood because there is no need to "type and crossmatch" prior to transfusion and thus save lives by saving time.

Specifically, the advantage over packed red blood cells include a predicted storage life of greater that two years contrasted with five weeks for whole blood. In addition, there is no need to crossmatch; transfusions can be started as soon as an IV is established rather than waiting until crossmatched blood is available. This is a minimum time savings of 45 minutes.

The hemoglobin of this invention is superior to existing perfluorochemicals because it will deliver adequate volumes of oxygen found in room air at 1 atm. pressure rather that 75% O$_2$. In addition, some patients are sensitized to perfluorochemicals, thus requiring a test dose for all recipients prior to receiving a transfusion with a ½ hour additional time delay.

An embodiment of this invention described above, FPSFH, has been shown superior to stroma-free hemoglobin with and without modification by pyridoxal-5'-phosphate because it has a greater intravascular retention time, half disappearance of 20 hours vs 3 hours, and it has superior oxygen transport capabilities not found in stroma-free hemoglobin with $P_{50}$ of 30 to 14 respectively.

In summary, the hemoglobin of this invention is a superior product for the rapid treatment of hypovolemic shock as experienced by combat casualty or civilian trauma because it can be used immediately by paramedical personnel to stabilize the victim. It is easy to prepare, has a long storage life and delivers oxygen to perfuse tissue when the victim is inhaling room air.

The hemoglobin of this invention is designed to resuscitate combat casualties suffering from hypovolemic shock. It is superior to perfluorochemicals because of its ability to carry oxygen when the victim is ventilated with room air.

It may be used in many important situations other than combat casualty and the treatment of hypovolemic shock. It would be an ideal substitute for whole blood used to prime the extracorporeal pumps used in cardiac bypass surgery. It also could be used to treat acute myocardial infarcts and cerebral vascular accidents and other ischemic episodes including prevention of sludging and pain in sickle cell crisis. It could be used as a cadaver organ perfusate to maintain organ viability until transplanted.

The preparation of crosslinked, modified stroma-free tetrameric hemoglobin of this invention is novel in that it uses a single intramolecular bifunctional reagent to crosslink the subunits of mammalian T state or deoxy hemoglobin to prevent the dissociation of $\alpha_2\beta_2$ to become $2\alpha\beta$, increase intravascular retention, and stabilize the T state hemoglobin configuration.

According to a preferred embodiment of this invention where covalent modification with pyridoxal-5'-phosphate is subsequent to the crosslinking reaction with a bis-diaspirin ester, the T state hemoglobin configuration is further enhanced by the reduction of pyridoxal-5'-phosphate on the beta $val_1$ alpha amino group.

Furthermore, the crosslinking and subsequent modification are specific, with product yields greater than 90% obtainable, require only reagents that are commercially available or easily synthesized, and allow preparation in large quantities. The produced hemoglobin of this invention may be lyophilized without changing its oxygen-transporting properties as a potential resuscitation fluid upon reconstitution. The unique modified hemoglobin has been purified and subsequently analyzed by HPLC and the crosslink was found between the beta chains.

A preferred derivative, FPSFH or fumarate-pyridoxalated hemoglobin referred to above, sustained life in five rats that were 95% exchanged-transfused with the solution. Preliminary in vivo tests support this derivative as a desirable oxygen-transporting resuscitation fluid.

DETAILED DESCRIPTION OF THE INVENTION

Description of Materials Used

Stroma-free hemoglobin solutions from various mammalian species are prepared starting with erythocytes in freshly drawn, outdated, or frozen packed cells or whole blood. The blood is drawn in a sterile fashion into containers with sufficient anticoagulant activity to prevent clot formation. Human blood, either freshly drawn from paid volunteers or outdated packed cells, meet all of the requirements for transfusion into human recipients established by the American Association of Blood Banks and is thus free of hepatitis and abnormal hemoglobins especially hemoglobin S.

Stroma-free hemoglobin from a variety of mammalian sources such as human, bovine, ovine or porcine can be used. Generally speaking, stroma-free hemoglobin, with the stromal elements removed still contains about 5% non-heme protein which preferably needs removal prior to crosslinking and modification according to this invention.

Generally, crystallizaton of the hemoglobin by methods in the literature, appropriate for each source of hemoglobin, is sufficient to remove this non-heme protein. However, for purposes of this invention, a preferable substrate is a stroma-free, non-heme protein free hemoglobin prepared by a zinc-precipitation method described as follows. This method, it is to be understood, while discussed specifically below with regard to hemoglobin derived from a human, is applicable to a variety of hemoglobins within the scope of this invention including those referred to above.

The preparation of hemoglobin free of greater than 98% of the non-heme protein found in the erythrocyte can be accomplished by precipitation of the hemoglobin as a zinc complex by the addition of a zinc salt such as zinc acetate to a dilute hemoglobin solution with a pH between 7.2 and 7.6. This preparation is the subject of a copending U.S. patent application by this inventor filed on even date herewith and entitled "Preparation of Stroma-Free, Non-Heme Protein-Free Hemoglobin", the contents of which are hereby incorporated-by-reference.

The precipitation of hemoglobin by zinc ion at a 10:1 Molar ratio indicates a specific high affinity ligand relationship for these two ions. This uniqueness is unlike ammonium sulfate or ethanol protein precipitation which organizes the water molecules in solution and excludes the protein, resulting in precipitation. The zinc hemoglobin complex is able to satisfy all the charge interactions without solvent interaction and precipitates without changing the environment for all of the protein molecules in general. It is thus unique and specific for hemoglobin.

Hemoglobin may be released from the erythrocyte by hypotonic lysis in twenty volumes of deionized water. Other methods of erythrocyte lysis such as "slow hypotonic lysis" or "freeze thaw", may also work well. The stroma is removed by ultrafiltration of the hemolysate on a 0.5 filter which retains the cellular components and passes the hemoglobin. This step is performed at 4° C. as rapidly as possible after hemolysis of the erythrocyte. Other methods of removing stroma are also acceptable.

The dilute solution of filtered hemoglobin or similar stroma-free hemoglobin solution prepared by other methods should again be filtered through a filter large enough to pass the hemoglobin but small enough to retain virus particles, protein aggregates and stromal elements. Such a filter has a nominal pore size of $0.020\mu$ and an exclusion for globular proteins of 1,000,000 Daltons. The solution is then adjusted to have a final pH of 7.5 with $MNa_2HPO_4$, 100 mM sodium chloride, and a hemoglobin concentration less than 0.5 percent. Other ions may be used as buffers, but the ions must not form precipitates with zinc ion.

At least ten moles of Zn ion are added per mole of hemoglobin. The addition is dropwise with stirring to allow a complete precipitation. The suspension is allowed to stir for fifteen minutes at temperature from 4°-37° C. Higher temperatures make the precipitate easier to collect but are unnecessary but may cause denaturation of the hemoglobin.

The precipitate is concentrated by filtration on a Pellicen Cassette HVLP $0.5\mu$ and the non-heme protein is removed in the filtrate. The hemoglobin is washed with 10 volumes of normal saline prior to resuspension by the addition of one mole of zinc chelating agent such as EDTA per mole of zinc added and sufficient volume of saline solution to achieve a 14% solution or less as desired. Removal of Zinc and EDTA is accomplished by dialysis.

After dialysis the pH of the material is adjusted to 7.40 with 0.1M HCL or NaOH and sterile filtered using an 0.22 filter into a sterile container.

The bis-diaspirin-esters are prepared according to conventional methods such as described in Wood et al., *J. Biol. Chem.*, 256, 7046 (1981). Pyridoxal-5'-phosphate and sodium borohydride were obtained from Sigma Chemical Company, and stored as directed by the supplier. All other reagents were of analytical grade or better. Deionized water (Millipore Super Q) was used throughout these experiments.

Description of Synthesis

Reference may be had to the following series of steps for an overview of the processes involved in the synthesis of a modified crosslinked stroma-free tetrameric hemoglobin of this invention using a preferred crosslinking agent, bis(3,5-dibromosalicyl)fumarate (BDBF).

Step 1. Stroma Free Oxy Hemoglobin (SFOH)
a. hemoglobin conc 1-14%, normal saline pH 7.40, temp 37° C.
b. remove bound and dissolved oxygen from solution of hemoglobin by subjecting sample to vacuum (35 mmHg) and nitrogen (760 mm) with agitation to less than 1 mm Hg.
c. Sample left under nitrogen pressure.

Step 2. Stroma Free Deoxy Hemoglobin (SFH)
a. adjust pH to 7.4
b. add BDBF (molar ratio to SFH 1.1:1) at 37° C., 2 hours, stirring under nitrogen positive pressure.

Step 3. Fumaryl Crosslinked Stroma Free Deoxy Hemoglobin (FSFH).
a. add pyridoxal-5-phosphate molar ratio to SFH 4:1 for one hour at 25° C. with stirring under nitrogen positive pressure.
b. add $NaBH_4$ molar ratio of SFH 20:1 for one hour at 20° C. with stirring under positive nitrogen pressure.

Step 4. Fumaryl Pyridoxal Stroma-Free Hemoglobin (FPSFH)
a. dialyze and prepare for storage.

The reaction of hemoglobin with BDBF was carried out in a 16-liter closed container (New Brunswick Scientific Microgen Fermenter) that had 4 to 12 liters of a 1 to 14% hemoglobin solution. Multiple entry sites in the top of the container allowed for introduction of an oxygen-purging inert gas bubbled into the solution and removal of dissolved gassed by vacuum. Continuous measurements of pH, $ppO_2$, and temperature were also performed through these entry sites. Liquid reagents were added with a syringe through a rubber septum to adjust the pH and initiate modification of the hemoglobin. The hemoglobin solution was sequentially subjected to a vacuum and flushed with inert gas until the oxygen tension of the solution was less than 1.0 mm Hg and the pH adjusted to 7.40 at 37° C. prior to addition of BDBF. BDBD (1.1M/1.0M of hemoglobin) was added as a solid reagent. The initial temperature, pH and partial pressure of oxygen were maintained throughout the two hour reaction. Agitation was maintained by a mechanical stirrer under constant nitrogen purge and caprylic alcohol was added as a defoamer.

The deoxygenated crosslinked hemoglobin was immediately modified with pyridoxyl-5'-phosphate without intermediate isolation of the crosslinked hemoglobin from the reaction mixture. The temperature was reduced to 25° C. and 5 moles of pyridoxyl-5'-prosphate per mole stroma-free Hb were added in 20–100 ml of deoxygenated 1M Tris pH 8.0. The equilibrium portion of the reaction proceeded for one hour at pH 7.40, prior to the addition of 5 moles of $NaBH_4$/mole of SFH in 20–200 ml of deoxygenated $10^{-3}$NaOH. After another two hours the reaction was terminated by exhaustive dialysis of the FPSFH against normal saline using ultrafiltration on a Millipore Pellicon, PTGC, membrane cassette. Dialysis was considered at equilibrium when 10 volumes of normal saline were removed as ultrafiltrate to yield the desired FPSFH in a form to be used as a blood substitute.

This exemplary process may be applied with appropriate modifications, evident to the skilled artisan from this disclosure, to the synthesis of addition of modified crosslinked hemoglobins within the scope of this invention.

Generally, the molar ratio of bis-diaspirin ester to tense state tetrameric hemoglobin is 1 to about 3, preferably about 1.1 to 1. The ratio of pyridoxal-5'-phosphate to tense state tetrameric hemoglobin is at least 1 to about 6, molar ratios greater than 6 being considered superfluous. A useful pH range is considered to be between about 7.2 to 8.5, about 7.4 being preferred. A useful temperature range for the crosslinking and modifying reactions of this invention is considered to be between room temperature and an upper limit of about 50° C.

However, it is essential to the successful practice of syntheses of modified crosslinked hemoglobin with the scope of this invention that crosslinking T state hemoglobin with the bis-diaspirin compounds as well as the modification with pyridoxal-5'-phosphate be conducted in the complete absence of oxygen measured by a partial pressure of oxygen less than 1 mm Hg so that the concentration of T state hemoglobin is greater than 97 percent of the total hemoglobin. This ensures that the product is primarily in the T state and has a low oxygen affinity.

Molecular weight determinations of the crosslinked hemoglobin molecule were made with a vertical 1.5 mm acrylamide gel slab (LKB) and the conditions specified by Walder et al (1979). This method has the unexplained ability to separate the alpha and beta monomeric subunits of hemoglobin. High pressure liquid chromatography (HPLC) analysis of the crosslinking reaction were carried out on a Water Peptide Analyzer with variable UV-visible adsorption detector, integrator and plotter. Preparative HPLC was performed by using a 4.1×250 mm Brownlee Aquapore AX300 column that was equilibrated with 0.02M Tris acetate pH 7.6 and developed with a linear gradient to a final concentration of 0.25M potassium acetate at 1 ml/minute for 30 minutes.

Description of Results

The reaction products of hemoglobin with BDBF at pH 7.40, 37° C. in normal saline are highly dependent upon the presence or absence of a heme ligand such as oxygen. Under low oxygen tensions in the absence of other heme ligands, the reaction proceeded to yield a mixture of three components separated as shown in FIG. 1. Peak I coincided with the retention time for control hemoglobin A. Peaks II and III were heme containing proteins which are more acidic that hemoglobin and more avidly bound to the anion groups of the matrix.

FIG. 1 describes the separation of hemoglobin products after reaction with BDBF on Aquapore AX300 as described. One milliliter fractions were collected as indicate. Fractions containing material with absorbance at 415 nm were obtained as indicated by the solid bars.

The amount of crosslink present in each of the hemoglobin products prepared by high pressure liquid chromatography (HPLC) was determined by SDS gel electrophoresis as shown in FIG. 2. Only Peak II, with the absence of the beta chains in the 17,000 dalton area and the formation of a new band at approximately 30,000 daltons, indicated the formation of a beta-beta dimer with a fumarate bridge. Peak I and III showed no material in the 30,000 dalton range; Peak I, unchanged from control and Peak III, with a more rapidly moving beta band, was consistent with modified but not crosslinked monomers.

FIG. 2 describes the SDS acrylamide gel electrophoresis of hemoglobin products after reaction with BDBF and purification by HPLC as indicated in FIG. 1. (a) hemoglobin control $\alpha$ and $\beta$ refers to hemoglobin monomer chains and CA=carbonic anhydrase, (b) Pool I material containing fractions 9 and 10, (c) molecular weight calibration mixture with molecular weights×1000 as indicated, (d) pool II material containing fractions 12 and 13, (e) Pool III material containing fractions 16 and 17.

The hemoglobin oxygen-dissociation curves for deoxyhemoglobin crosslinked with BDBF (FSFH) and purified FSFH reacted with PLP (FPSFH) are shown in FIG. 3. For comparative purposes, oxyhemoglobin crosslinked with BDBF ($O^2HbXL$) (Walder et al., 1979), unmodified hemoglobin A, and whole blood are included. FIG. 3: Hemoglobin oxygen dissociation curves, at 37° C., pH 7.4, 0.15M NaCl. $O^2HbXL$ ($P_{50}=9$ mm Hg); FSFH ($P_{50}=18$ mm Hg); FPFSH ($P_{50}=32$ mm Hg); HbA, stroma-free hemoglobin prepared by zinc ion precipitation ($P_{50}=14$ mm Hg); blood, freshly drawn normal human donor ($P_{50}=29$ mm Hg).

Complete exchange transfusions with the FPSFH of this invention were performed in five rats to a final hematocrit less than 2 percent, according to the technique of DeVenuto et al., Transfusion, 17, 555 (1977). One rat was infused with identical hemoglobin material that was lyophilized and reconstituted with sterile water prior to exchange transfusion. Control rats (n=5) were exchange transfused with albumin, and another group with stroma-free hemoglobin A (n=5). The albumin recipients were all dead at 45 minutes, while the stroma-free hemoglobin recipients were all dead at 5½ hours. All of the rats receiving FPSFH lived until they were sacrificed at 7 days for necropsy. The rat receiving the lyophilized material died at 47 hours, with a clinical and pathological diagnosis of sepsis.

At this time, conclusive evidence about its pharmacokinetics is not available but preliminary results showed a 20-hour half-disappearance time when it was given to a rabbit in a small dose (200 mg/kg).

Discussion of Results

Stroma-free hemoglobin can be modified with BDBF under conditions described to yield a specific beta-beta crosslinked T state hemoglobin molecule with a low oxygen affinity and significant intravascular retention. The derivative (FSFH), is chemically defined and unique as judged by chromatography and acrylamide gel electrophoresis. A significant decrease in oxygen affinity can be realized by the subsequent reaction of the crosslinked hemoglobin with pyridoxal-5'-phosphate. This combination produces a hemoglobin oxygen-dissociation curve virtually identical to whole blood.

The reaction conditions to produce modified hemoglobin have been optimized by analyzing the amount crosslink present in mixtures made under controlled conditions (pH, $ppO_2$, temperature, ionic strength) by the techniques used. We have attempted to optimize yields; and to define the reaction products. On the basis of these results it is now possible to reproduce the modification of hemoglobin with yields approximately 95% and to insure product uniformity.

The precise location of the intramolecular modification is unknown, but circumstantial evidence implicates a $beta_1 val^1$-$beta_2 lys^{82}$ bridge. On SDS gels and analytical HPLC it is clear that the beta chains are involved in formation of the stabile dimer, and it is not possible to crosslink hemoglobin that has PLP on both beta $val^1$ positions. The possibility that beta $lys^{82}$ to beta $lys^{82}$ was crosslinked is unlikely because of the substantially different oxygen affinity between $O^2HbXL$ and FSFH or FPSFH. $O^2HbXL$ is formed by crosslinking oxy HbA with BDBF to yield a $beta_1 lys^{82}$-$beta_2 lys^{82}$ (Walder et al., 1980). Because it is possible to have hemoglobin both fumarate-crosslinked and pyridoxal-modified, and because it is necessary to consider the distance to bond the crosslinking agent in the T state, the evidence is consistent with the implication of a beta $val^1$-beta $lys^{82}$ bridge.

This approach shows that human deoxyhemoglobin can be easily crosslinked and modified to a specific product in large quantities. The product shows promise of being a good candidate for an oxygen-transporting resuscitation solution.

Variations of the embodiments of this invention as disclosed above will be apparent to the skilled artisan. These modifications are to be considered within the scope of the claims to this invention which follow.

I claim:
1. Stroma-free tense state tetrameric mammalian hemoglobin covalently crosslinked with a diamide bond-forming moiety derived from a bis-diaspirin ester and covalently modified with pyridoxal-5'-phosphate, wherein said pyridoxal-5'-phosphate covalent modifying bond is reduced, and wherein said crosslinking and modifying covalent bonds occur in the beta cleft.

2. Stroma-free tetrameric hemoglobin according to claim 1 wherein the hemoglobin is derived from a human.

3. Stroma-free tetrameric hemoglobin according to claim 1 wherein the hemoglobin is bovine, ovine or porcine.

4. Stroma-free tetrameric hemoglobin according to claim 2 wherein the bis-diaspirin ester is bis(3,5-dibromosalicyl)-fumarate.

5. Stroma-free tetrameric hemoglobin according to claim 4 wherein the beta cleft covalent crosslinking occurs between the alpha amino group of beta$_1$ Val$_1$ and the epsilon amino group of beta$_2$ Lys$_{82}$.

6. Stroma-free tetrameric hemoglobin according to claim 2 wherein the bis-diaspirin ester is bis(3,5-dibromosalicyl)-succinate.

7. Modified crosslinked stroma-free tense state tetrameric mammalian hemoglobin prepared by a process comprising sequentially allowing stroma-free tetrameric hemoglobin in the tense state to covalently react with a bis-diaspirin ester and pyridoxal-5'-phosphate, said reaction with pyridoxal-5'-phosphate being followed by reduction of the reversible Schiff base covalent bond.

8. The stroma-free tetramic hemoglobin of claim 7 wherein the hemoglobin is derived from a human.

9. The stroma-free tetrameric hemoglobin of claim 8 wherein the covalent crosslinking reaction of tense state hemoglobin with the bis-diaspirin ester is followed by the covalent modification of the crosslinked hemoglobin by pyridoxal-5'-phosphate.

10. The stroma-free tetrameric hemoglobin of claim 9 wherein the bis-diaspirin ester is bis(3,5-dibromosalicyl)-fumarate.

11. The stroma-free tetrameric hemoglobin of claim 9 wherein the bis-diaspirin ester is bis(3,5-dibromosalicyl)-succinate.

12. Stroma-free tense state tetrameric mammalian hemoglobin covalently crosslinked with the diamide bond-forming moiety having the structure

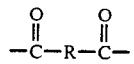

wherein R has a chain length of 1, 2, 3 or 4 units selected from —CH— and —CH$_2$—, said diamide bond-forming moiety derived from a bis-diaspirin ester, the diaspirin moiety having the structure

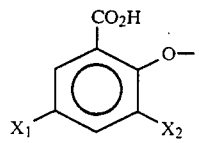

wherein X$_1$ and X$_2$ are selected from —H, —Br, —I, —NO$_2$ and wherein either X$_1$ or X$_2$, or both, are present, said stroma-free tense state tetrameric hemoglobin additionally covalently modified with pyridoxal-5'-phosphate, wherein said pyridoxal-5'-phosphate covalent modifying bond is reduced, and wherein said crosslinking and modifying covalent bonds occur in the beta cleft.

13. Stroma-free tetrameric hemoglobin according to claim 12 wherein the hemoglobin is derived from a human.

14. Stroma-free tetrameric hemoglobin according to claim 13 wherein the bis-diaspirin ester is bis(3,5-dibromosalicyl)-fumarate.

15. Stroma-free tetrameric hemoglobin according to claim 13 having an oxygen partial pressure in the range of 25 to 35 mm Hg.

16. Stroma-free tetrameric hemoglobin according to claim 15 having an oxygen partial pressure of about 30 mm Hg.

17. Stroma-free tetrameric hemoglobin according to claim 12 lyophilized and suitable for reconstitution to an oxygen-carrying resuscitation fluid.

18. A process for the preparation of modified crosslinked stroma-free tense state tetrameric mammalian hemoglobin comprising reducing the oxygen tension of a solution of stroma-free hemoglobin to a value less than 1 mm Hg to thereby maximize presence of tense state hemoglobin, then sequentially allowing said stroma-free tense state tetrameric hemoglobin to covalently react with a bis-diaspirin ester and pyridoxal-5'-phosphate, said reaction with pyridoxal-5'-phosphate being followed by reduction of the reversible Schiff base covalent bond.

19. A process according according to claim 18 wherein the hemoglobin is derived from a human.

20. A process according to claim 19 wherein the covalent crosslinking reaction of tense state hemoglobin with the diaspirin ester is followed by the covalent modification of the crosslinked hemoglobin by pyridoxal-5'-phosphate.

21. A process according to claim 20 wherein the bis-diaspirin ester is bis(3,5 dibromosalicyl)-fumarate.

22. A method for treating a mammal for blood loss or ischemia comprising administering to the mammal a therapeutic amount of a modified crosslinked stroma-free tense state tetrameric hemoglobin, wherein said tetrameric hemoglobin is covalently crosslinked with a bis-diaspirin ester and covalently modified with pyridoxal-5'-phosphate in the beta cleft, and wherein said pyridoxal-5'-phosphate covalent modifying bond is reduced.

23. A method according to claim 22 wherein the mammal is a human, the stroma-free tetrameric hemoglobin is non-heme protein-free derived from a human, and the bis-diaspirin ester covalent crosslinking bond in derived from bis(3,5 dibromosalicyl)-fumarate.

* * * * *